United States Patent [19]

Busch et al.

[11] Patent Number: 5,380,860

[45] Date of Patent: Jan. 10, 1995

[54] PREPARATION OF BETA-KETOESTERS USEFUL IN PREPARING QUINOLONE ANTIBIOTICS

[75] Inventors: Frank R. Busch; Richard S. Lehner; Brian T. O'Neill, all of New London, Conn.

[73] Assignee: Pfizer Inc., New York, N.Y.

[21] Appl. No.: 826,285

[22] Filed: Jan. 24, 1992

Related U.S. Application Data

[63] Continuation of Ser. No. 500,155, Mar. 27, 1990, abandoned.

[51] Int. Cl.$^6$ .................... C07C 67/14; C07D 213/55
[52] U.S. Cl. ........................................ 546/315; 560/51
[58] Field of Search ........................... 546/315; 560/51

[56] References Cited

U.S. PATENT DOCUMENTS

| | | | |
|---|---|---|---|
| 4,599,334 | 7/1986 | Peterson et al. | 514/253 |
| 4,611,080 | 9/1986 | Grohe | 560/51 |
| 4,833,270 | 5/1989 | Bitha et al. | 562/493 |
| 5,045,549 | 9/1991 | Sauter et al. | 514/312 |

FOREIGN PATENT DOCUMENTS

| | | |
|---|---|---|
| 078362 | 5/1983 | European Pat. Off. |
| 0251308 | 1/1988 | European Pat. Off. |
| 0303291 | 2/1989 | European Pat. Off. |
| 342849A3 | 11/1989 | European Pat. Off. |
| 342849 | 11/1989 | European Pat. Off. |
| 345998A1 | 12/1989 | European Pat. Off. |
| 2170804 | 8/1986 | United Kingdom . |
| 9102526 | 3/1991 | WIPO . |

OTHER PUBLICATIONS

Clay, R. J. et al., "A Safe, Economical Method for the Preparation of β-Oxo Esters," *Synthesis*, pp. 290-292 (1993).
Wemple, 1989, International Chemical Congress of Pacific Basin Societies.
House, Dr. H. O., "Acylation at Carbon," Modern Synthetic Reactions, Benjamin Menlo Park, (1972).
Ireland, R. E. et al., "A New Synthetic Method for the Preparation of α-Substituted β-Ketoesters," *J. Am. Chem. Soc.*, 81, p. 2907 (1959).
Lienhard, G. E. et al., "The Reaction of Carbanions with N,S–Diacetylcysteamine. A Model for Enzymatic Carbon–Carbon Condensation," *J. Am. Chem. Soc.*, 87, pp. 3863-3874 (1965).
Oikawa, Y. et al., "Meldrum's Acid in Organic Synthesis. 2. A General and Versatile Synthesis of β-Keto Esters," *J. Org. Chem.*, 43, p. 2087 (1978).
Scott, A. Ian et al., "Acetyl Transfer Reaction in Catechol Acetate malonate. A Model for the Biosynthesis of Polyketides and Fatty Acids," *J. Am. Chem. Soc.* 97, pp. 6277-6278 (1975).
Staab, H. A. et al., "Darstellung von Imidazoliden. Synthese von Amden, Hydraziden und Hydroxamsauren nach der Imidazolidmethode," *Chem. Ber.*, 95, pp. 1275-1283 (1962).
Chu et al. "Synthesis and Structure–Activity Relationships of New Arylfluoronaphthyridine Antibacterial Agents". *J. Med. Chem.*, vol. 29, No. 11 (1986).
Pollet et al., Syntheses, 142-143 (1978).
Brooks et al., Angew. Chem., Int. Ed. Engl., 18, 72-74 (1979).
Wierenga et al., J. Org. Chem., 44, 310-11 (1978).
Wierenga et al., J. Organic Syntheses, 61, 5-8 (1980).
Wentrup et al., J. Am. Chem., Soc., 102, 6161-63 (1980).
Rathke et al., J. Org. Chem., 50, 2622-24 (1985).
Wemple, (1989), International Chemical Congress of Pacific Basin Societies.
Bram et al., Bull. Soc. Chem. Francais, pp. 945-951 (1964).

*Primary Examiner*—Bernard Dentz
*Attorney, Agent, or Firm*—Peter C. Richardson; Paul H. Ginsburg; Philip C. Strassburger

[57] ABSTRACT

A method for preparing a compound of the formula

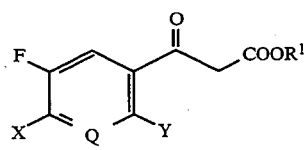

I (Abstract continued on next page.)

wherein Q is C—H or N; $R^1$ is $C_1$–$C_4$ alkyl, benzyl or p-nitrobenzyl and X and Y are independently selected from fluoro and chloro comprising reacting a compound of the formula

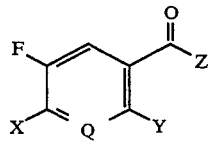

III wherein Q is >C—H or N; X and Y are independently selected from fluoro and chloro; and Z is fluoro, chloro, 1-imidazolyl or substituted 1-imidazolyl, wherein the 1-imidazolyl group is substituted with one or two substituents independently selected from $C_1$ to $C_4$ alkyl, with a compound of the formula

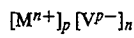

wherein M is an alkaline earth metal, Cu or Mn, n is 2, $V^{p-}$, wherein p is 1 or 2, is an anion of the formula

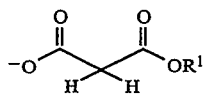

V(a)

or a dianion of the formula

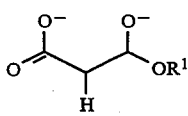

V(b)

and $R^1$ is $C_1$ to $C_6$ alkyl or paranitrobenzyl, with the proviso that when Z is 1-imidazolyl or substituted 1-imidazole, M is magnesium, copper or manganese and with the proviso that when Z is fluoro, chloro or bromo, $V^{p-}$ is a dianion of the formula V(b).

7 Claims, No Drawings

PREPARATION OF BETA-KETOESTERS USEFUL IN PREPARING QUINOLONE ANTIBIOTICS

This is a continuation of application Ser. No. 07/500,155, filed on Mar. 27, 1990 now abandoned.

BACKGROUND OF THE INVENTION

The present invention relates to the preparation of beta-ketoesters useful in preparing quinolone antibiotics.

European Patent Application Publication Number 0215650 discloses quinolone antibiotics, including 1-cyclopropyl-6-fluoro-1,4-dihydro-7-(1S:4S)-5-methyl-2,5-diazabicyclo-[2.2.1]hept-2-yl-4-oxo-3-quinoline-carboxylic acid (danofloxacin), a quinolone being developed for animal health use, and 1-cyclopropyl-6-fluoro-1,4-dihydro-7(1S:4S)-8-methyl-3,8-diazabicyclo-[3.2.1]oct-3-yl-4-oxo-3-quinoline-carboxylic acid, International Application No. PCT/US89/03489, filed Aug. 16, 1989, discloses 7-azabicyclo-substituted quinolone carboxylic acids having antibacterial activity.

European Patent Application 89304697.9 discloses compounds of the formula

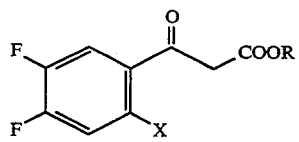

wherein R is $C_1$–$C_4$ alkyl and X is fluoro, chloro or bromo as intermediates for preparing quinolone antibiotics. The compounds are prepared by reacting 2-halo-4,5-difluoro-acetophenone, wherein halo is fluoro, chloro or bromo, with a strong base and then reacting the resulting anion with a $C_1$–$C_4$ alkyl cyanoformate. Alternatively, 2-halo-4,5-difluorobenzoyl chloride, wherein halo is fluoro, chloro or bromo, is reacted with the dilithium salt of a mono ($C_1$–$C_4$) alkyl malonate.

P. Pollet and S. Gelen, *Synthesis*, 142–143 (1978) refer to the reaction of monoethyl malonate with isopropyl magnesium bromide followed by addition of an acid chloride of the formula

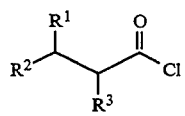

to give a beta-keto ester. Pollet and Gelen used acid chlorides wherein $R^1$ was hydrogen or methyl; $R^2$ was hydrogen, methyl or —$COOC_2H_5$; and $R^3$ was hydrogen or methyl.

D. W. Brooks et al. *Angew. Chem. Int. Ed. Engl.*, 18, 72–74 (1979) refer to the reaction

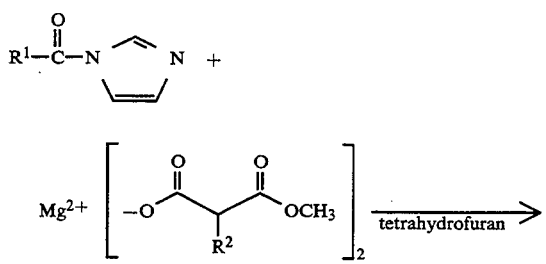

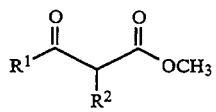

wherein $R^1$ is selected from phenyl, phenylethyl, and a variety of saturated and unsaturated straight chain hydrocarbon groups, and $R^2$ is hydrogen or methyl.

T. N. Salzmann et al., *J. Am. Chem. Soc.*, 102, 6161–6163 (1980), refer to the reaction of a compound of the formula

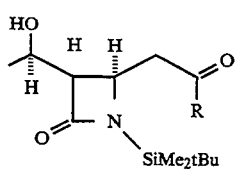

wherein R is imidazolyl with the magnesium salt of the mono para-nitrobenzyl ester of malonic acid in tetrahydrofuran at room temperature to provide a betaketoester.

M. W. Rathke and P. J. Cowan, *J. Org. Chem.*, 50, 2622–2624 (1985) refer to C-acylation of diethyl malonate with acid chlorides in the presence of magnesium chloride and pyridine or triethylamine.

J. Wemple, 1989 *International Chemical Congress of Pacific Basic Societies*, refers to the following reaction for use in preparing 6-fluoroquinoline antibacterial agents:

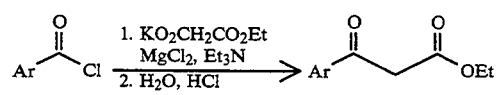

wherein Ar phenyl; 3,4-dichlorophenyl; 2,4,5-trifluoro-3-chlorophenyl; pentafluorophenyl; 2,3,4,5-tetrafluoro-6-nitrophenyl; or p-methoxyphenyl.

SUMMARY OF THE INVENTION

The present invention relates to a method for preparing a compound of the formula

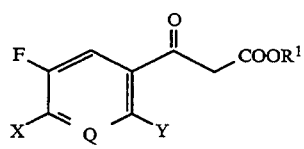

wherein Q is C—H or N; $R^1$ is $C_1$ to $C_4$ alkyl, benzyl or p-nitrobenzyl and X and Y are independently selected from fluoro and chloro comprising reacting a compound of the formula

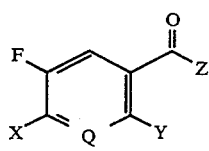

wherein Q is C—H or N; and Y are independently selected from fluoro and chloro and Z is fluoro, chloro, bromo, 1-imidazolyl or substituted 1-imidazolyl, wherein the 1-imidazolyl group is substituted with one or two substituents independently selected from $C_1$ to $C_4$ alkyl (preferably methyl), with a compound of the formula

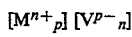

wherein M is an alkaline earth metal, Cu or Mn; n is 2; $V^{p-}$ wherein p is 1 or 2, is an anion of the formula

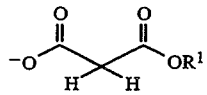

or a dianion of the formula 1-imidazolyl, M is magnesium, copper or manganese and with the proviso that when Z is fluoro or chloro, $V^{p-}$ is a dianion of the formula V(b).

The present invention also relates to compounds of the formula III wherein Q is C—H; Z is 1-imidazolyl or substituted 1-imidazolyl wherein the 1-imidazoyl group is substituted with one or two substituents independently selected from $C_1$ to $C_4$ alkyl; X is fluoro or chloro; and Y is fluoro or chloro.

DETAILED DESCRIPTION OF THE INVENTION

The following reaction schemes illustrate the processes of the present invention, the preparation of the compounds of the present invention, and the use of the compounds thus prepared to prepare quinolone antibiotics.

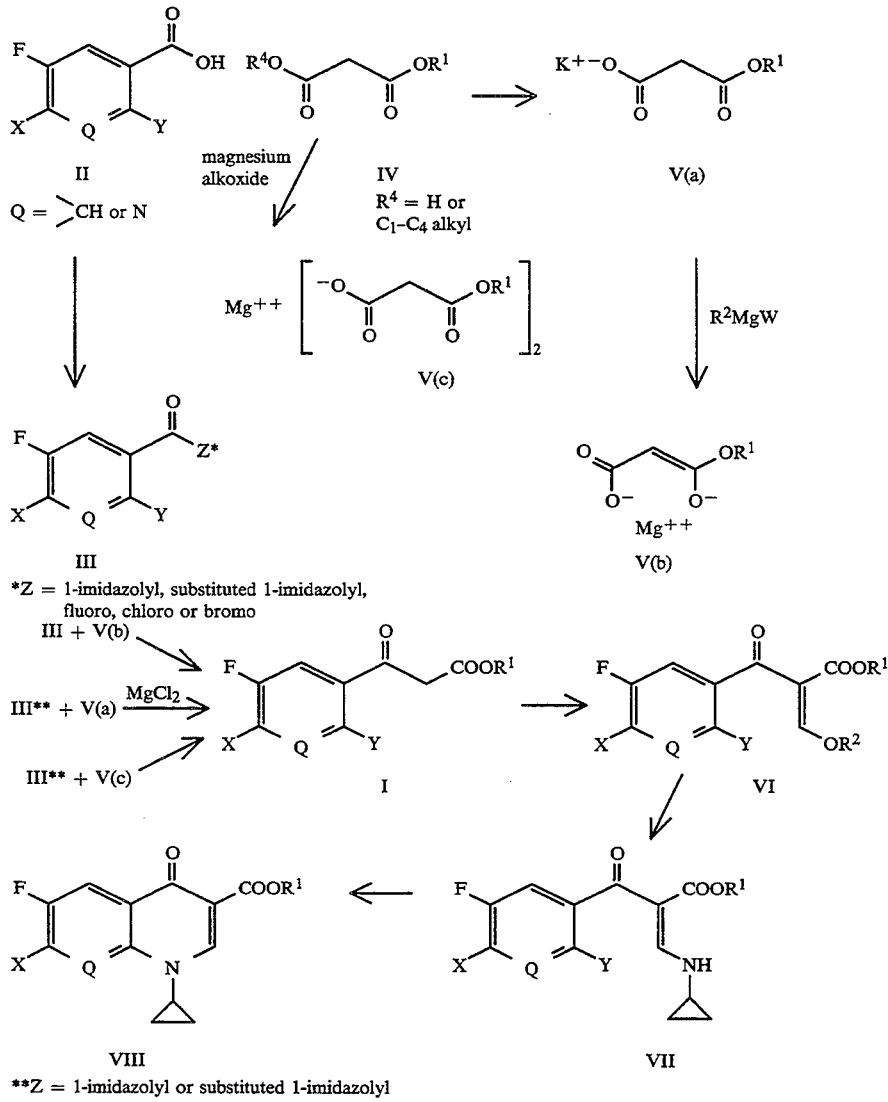

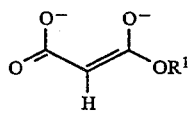

and $R^1$ is $C_1$ to $C_6$ alkyl, benzyl or p-nitrobenzyl; with the proviso that when Z is 1-imidazolyl or substituted Typically, the acid II is converted into the acyl imidazole III (Z=imidazolyl) by direct reaction with a reagent such as carbonyl diimidazole in an inert solvent such as methylene chloride, chloroform, tetrahydrofuran, ether, benzene or toluene at a temperature between about 0° to about 40° C., generally about 25° C., for a period of about 0.25 to about 2 hours, preferably 1 hour. Alternatively, the acyl imidazole III (Z=imidazolyl) may be prepared from the acid chloride III (Z=chloro) through the use of imidazole and a suitable base such as triethylamine or more conveniently with excess imidazole, in an inert solvent such as those described above, at a temperature between about −10° C. to about 25° C., preferably about 5° C. to about 10° C., for a period of 1 to 3 hours, preferably 1.5 hours.

Typically, the acid II is converted into the acid chloride III with a reagent capable of converting an acid to an acid chloride (e.g., thionyl chloride) in toluene or another inert solvent such as benzene, hexanes, or methylene chloride, at a temperature between about 50° and about 100° C., preferably at about 80° C., for a period of about 0.5 hours to about 8 hours, preferably about 2 hours. Other reagents useful for acid chloride formation such as oxalyl chloride, phosphorous oxychloride or phosphorous pentachloride may also be utilized, and a catalyst such as pyridine or dimethylformamide in an amount of about 0.5 mole percent may be added.

The acyl imidazole III may be converted to a beta-ketoester having the formula I through reaction with the magnesium, copper or manganese carboxylate salt of a suitable monoester of malonic acid in a solvent such as tetrahydrofuran, dimethoxyethane or the like at a temperature between about 25° to about 100° C., preferably about 67° C., for a period of about 3 to about 24 hours, preferably about 8 hours.

The magnesium salt may be prepared and isolated from a reaction between a suitable monoester of malonic acid (see, for example, European Patent Application 89304697.9) and reagents such as magnesium alkoxide (e.g., magnesium ethoxide, magnesium methoxide and the like) in an inert solvent such as ether or tetrahydrofuran, by known methods (see, for example, *Angew. Chem. Int. Ed. Engl.*, 18, 72–74 (1979) and *J. Am. Chem. Soc.*, 102, 6161–6163 (1980). One such reagent, p-nitrobenzylmalonate magnesium salt dihydrate, and the ethyl ester thereof are commercially available from Chemical Dynamics Corporation.

Alternatively, the magnesium carboxylate can be prepared in situ by the inclusion of a suitable magnesium salt, such as magnesium chloride, bromide or iodide and the like, with a more readily available carboxylate salt of a monoester of malonic acid, such as the potassium salt (which can be prepared as described in *Organic Synthesis*, Vol. IV, 417–419 (1963)) or the sodium and lithium salts, as well as others. The sodium and lithium salts can be prepared similarly to the potassium salt or by the reaction of $HO_2CCH_2CO_2CH_3$ with, respectively, sodium hydride in tetrahydrofuran or butyllithium in tetrahydrofuran. The potassium carboxylate salts of monoesters of malonic acid can also be prepared from the corresponding diesters by reacting the latter with potassium hydroxide in a solvent comprising water and an alcohol (e.g., methanol when $R^1$ is methyl or ethanol when $R^1$ is ethyl).

The copper and manganese carboxylate salts can be prepared in situ from the potassium salt in a manner similar to the in situ preparation of the magnesium carboxylate salt described above, by the inclusion of salts such as cupric chloride and manganic chloride, respectively.

Isolation of the beta-ketoester I is facilitated by converting it to its tautomer enol of the formula Ia as depicted below.

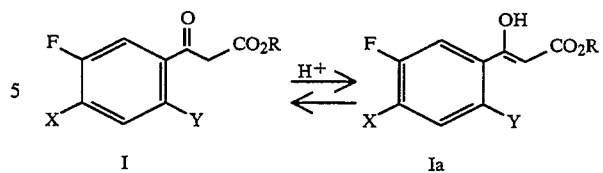

This can be done by simply treating a solution of the beta-ketoester I in a solvent such as ethyl acetate or, alternatively, methylene chloride, chloroform, ether, benzene, toluene or the like with an aqueous acid such as dilute hydrochloric acid or dilute sulfuric acid. The percentage of the enol tautomer may be analyzed by NMR spectroscopy. The enol tautomer crystalizes easily and makes isolation of the product more facile. The enol tautomer is also useful in preparing the compound of the formula VI from the compound of the formula I and in preparing the compound of the formula VIII from the compound of the formula VII.

Alternatively, the acid chloride III is reacted with a compound of the formula

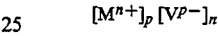

as defined above. As indicated above, $V^{p-}$ may be a dianion of the formula V(b). The dianion of the formula V(b) may be prepared by reacting the monoanion of the formula V(a) with a Grignard reagent of the formula $R^2MgW$ wherein $R^2$ is $C_1$ to $C_4$ alkyl or phenyl and W is chloro, bromo or iodo. If desired, preparation of the dianion can be conducted in situ.

As illustrated in the above reaction scheme, the acid chloride III may be reacted with the malonate compound of the formula V(b) to give a compound of the formula I. It is preferable to use 2 equivalents of the compound of the formula V(b) in order to obtain high yields. Typically, the compound of formula I is prepared by the initial formation of a magnesium malonate complex from the corresponding potassium alkyl (e.g. methyl or ethyl) or paranitrobenzyl malonate and alkyl magnesium halide (e.g., chloride) in tetrahydrofuran. The magnesium malonate complex can be formed from the corresponding potassium malonate ester, sodium malonate ester, or lithium malonate ester. The potassium malonate ester is preferred. The alkyl magnesium chloride can be about 4.0 to about 0.5 molar, but about 2 to about 3 molar is preferred. The magnesium malonate complex is then condensed with the acid chloride III at a temperature of about −5° C. to about the reflux temperature of the solution (i.e. about 67° C.). A temperature range of about 10° to about 40° C. is preferred. The reaction mixture is then quenched into an aqueous acid and extracted to give the desired compound of the formula I in high yield. The extraction can be done with methylene chloride, ethyl acetate, toluene or any suitable solvent. Toluene is preferred since residual water is removed azeotropically as the product is concentrated.

The compound of formula I, wherein $R^1$ is methyl or ethyl, Y is chloro and X is fluoro, can be transformed into 2-(2-chloro-4,5-difluoro benzoyl)-3-ethoxy acrylic acid ester (e.g. the methyl ester or ethyl ester) (VI), which can then be converted into the corresponding compound of the formula VII, by the procedure of Grohe et al. (European Patent Application Publication Number 0078362). Alternatively, compounds of the formula VII can be prepared from corresponding the compound of formula VI by dissolving the latter in a C$_5$ to C$_7$ cycloalkane, preferably cyclohexane, followed by the addition of cyclopropylamine in a C$_5$ to C$_7$ cycloalkane, preferably cyclohexane. Typically, the reaction temperature is controlled between about 20° and about 35° C., and stirring is continued for between about 1 and about 2 hours. The product of formula VII is isolated by filtration of the reaction mixture. It is then dissolved in an inert solvent such as tetrahydrofuran, dimethyoxyethane or dimethylformamide and treated with a strong base (e.g., potassium tert-butoxide or sodium hydride), at a temperature of about −10° C. to about 15° C. After the addition is complete, the reaction mixture may be heated to between about 50° and about 150° C. to provide the corresponding compound of the formula VIII, which may be 1-cyclopropyl-6,7-difluoro-1,4-dihydro-4-oxo-quinoline-3-carboxylic acid ester (e.g., methyl ester or ethyl ester). Removal of the ester protecting group from compounds of the formula VIII is conducted via acid hydrolysis, preferably in acetic acid, in the presence of about 1N to about 4N HCl. The suspension is heated to reflux for about 1.5 to about 3 hours to yield the acid wherein R$^2$ is hydrogen.

The compound of the formula VIII so formed may be used to prepare the antibacterial compound 1-cyclopropyl-6-fluoro-1,4-dihydroxy-4-oxo-7-(5-methyl-(1S,4S)-2,5-diazabicyclo[2.2.1]hept-2-yl)-quinoline-3-carboxylic acid, which is disclosed in European Patent Application Publication No. 0215650, by coupling the compound of the formula VIII wherein R is C$_1$-C$_4$ alkyl with the required side chain followed by hydrolysis or by first hydrolyzing a compound of the formula X wherein R is C$_1$-C$_4$ alkyl to the compound wherein R is hydrogen and then coupling with the required side chain.

The aforementioned antibacterial compound and similar antibacterial compounds that may be prepared using the compound of formula VIII are useful in the treatment of a broad spectrum of bacterial infections, particularly the treatment of infections caused by gram-positive bacterial strains. The antibacterial compounds may be administered alone, but will generally be administered in admixture with a pharmaceutical carrier selected with regard to the intended route of administration and standard pharmaceutical practice. For example, they can be administered orally or in the form of tablets containing suck excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5–5000 ppm, preferably 25–500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, the antibacterial compounds can be administered intramuscularly or subcutaneously at dosage levels of about 0.1–50 mg/kg/day, advantageously 0.2–10 mg/kg/day given in a single daily dose or up to 3 divided doses. The antibacterial compounds can be administered to humans for the treatment of bacterial diseases by either the oral or parenteral routes, and may be administered orally at dosage levels of about 0.1 to 500 mg/kg/day, advantageously 0.5–50 mg/kg/day given in a single dose or up to 3 divided doses. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art. The antibacterial activity of the compounds is shown by testing according to the Steer's replicator technique which is a standard in vitro bacterial testing method described by E. Steers et al., *Antibiotics and Chemotherapy*, 307 (1959).

The following Examples illustrate the preparation of the compounds of the present invention. All melting points referred to in the Examples are uncorrected.

Example 1

Ethyl-3-(2-chloro-4,5-difluorophenyl)-3-oxopropionate

A 400 liter glass-lined reactor was charged with 129 liters of dry tetrahydrofuran and 21.7 kg (2.1 equivalents) of potassium ethyl malonate. With slight cooling, 42.4 liters of 3M methyl magnesium chloride was added at a rate to keep the temperature between 20° to 50° C. After a 30 minute stir, the solution was cooled to 0° to −5° C. and 12.8 kg of 2-chloro-4,5-difluorobenzoyl chloride was added at a rate to keep the temperature between 0° and 5° C. The solution was then quenched into 106 liters of 2N HCl. After the addition of 72 liters of toluene, the aqueous layer was removed. The product layer was washed with 53 liters of saturated bicarbonate and salt solution. After removal of the aqueous layer, the product layer was concentrated to an oil and 28 liters of isopropyl alcohol were added. The solution was cooled to −10° to −15° C., granulated and the solids filtered and vacuum dried to give 14.17 Kg (first crop) and 588 g (second crop) of the title compound, 92.8% yield. The high field NMR of the product was typical of that for a mixture of the keto (5%) and enol (95%) forms of the title compound 300 MHz $^1$H (CDCl$_3$): 12.5 (s, 0.95H), 7.5 (d of d, J=11 Hz, J'=8 Hz, 1H) 7.3 (d of d, J=11 Hz, J'=8 Hz, 1H), 5.6 (s, 0.95H), 4.3 (q, J=6H, 1.9H), 4.2 (q, J=6 Hz, 0.1H), 4.0 (s, 0.1H), 1.4 (t, J=6 Hz,2.85H), 1.2 (t, J=6 Hz, 0.15H).

Example 2

Methyl-3-(2-chloro-4,5-difluorophenyl)-3-oxopropionate

A 400 liter glass-lined reactor was charged with 257 liters of tetrahydrofuran and 32.05 kg (205.2 moles, 2.1 eq) of potassium methyl malonate. While the reaction mixture was cooled to maintain the temperature below 40° C., 82.5 liters of 2.4M (198 moles, 2.02 eq) methyl magnesium chloride were added over about 1.5 hours. The addition resulted in a thick slurry of the malonate magnesium complex. The slurry was stirred for 0.5 hours at about 32° C. Then 2-chloro-4,5-difluorobenzoyl chloride (20.7 kg, 98.1 moles) was added with cooling, maintaining the temperature between 32° and 23° C. After the addition was complete, the turbid solution was stirred for 0.5 hours and was quenched into 154 l of 2N HCl. The product was extracted with 114 l of toluene. The organic layer was washed with 91 l of saturated sodium bicarbonate/sodium chloride solution. The product/organic layer held 2.5% water (by Karl Fischer titration) which was higher than usual (i.e. 0.5 to 1.5%), so it was washed with 76 l of saturated sodium chloride solution. The organic layer was concentrated by vacuum distillation to about 26 l and 28 l of isopropyl alcohol were then added. The product was crystallized by cooling to −10° to −12° C. The product was collected by filtration and then vacuum dried to give 22.3 kg (89.7 moles, 91.4 % yield) of the title compound. The high field NMR of the product was typical of that for a mixture of the keto (60%) and enol (40%) forms of the title compound. 300 MHz $^1$H NMR (CDCl$_3$): 12.4 (s, 0.4H), 7.5 (m, 1H), 7.3 (m, 1H), 5.6 (s, 0.4H), 4.0 (s, 1.2H), and the methyl esters 3.7 (s, 1.3H), 3.6 (s, 1.7H).

Example 3

Ethyl-3-(2,6-dichloro-5-fluoro)-oxo-3-pyridinepropionate 2,6-Dichloro-5-fluoropyridine-3-carboxylic acid (5.22 g, 25 mmol) was treated with thionyl chloride (10 ml) and heated to reflux for 18 hours. The thionyl chloride was then removed in vacuo, and the residue slurried in acetonitrile, which was also removed at reduced pressure. The resulting brown oil was dissolved in tetrahydrofuran (10 ml).

Methylmagnesium chloride (3N solution in tetrahydrofuran, 17.5 ml, 52.5 mmol) was added dropwise to a solution of potassium monoethyl malonate (9.0 g, 53 mmol) in tetrahydrofuran (50 ml), such that the temperature of the reaction mixture did not rise above 40°. After completion of the addition, the mixture was heated at 50° for 0.5 hour. After being cooled to 0°, the malonate solution was treated dropwise with the tetrahydrofuran solution of the acid chloride prepared above, and the resulting mixture was allowed to stir for 1 hour at room temperature. Hydrochloric acid (1N, 100 ml) and ethyl ether (100 ml) were added, and the layers separated; the organic layer was washed with aqueous sodium bicarbonate and saturated aqueous sodium chloride solution, dried over sodium sulfate, filtered and concentrated in vacuo to provide a yellow-brown oil. Purification by column chromatography (eluant: 20% ethyl acetate in hexanes) provided the title product as a white solid, mp 71°–72° (4.26 g, 15.2 mmol, 61% yield). $^1$H NMR (CDCl$_3$, mixture of keto and enol forms): 12.55 (s, 1H, enol form), 7.81 (d, J=7 Hz, 1H), 5.81 (s, 1H, enol form), 4.27 and 4.17 (q, J=7 Hz, 2H), 4.07 (s, 2H, keto form), 1.32 and 1.24 (t, J=7 Hz, 3H).

Example 4

2-Chloro-4,5-difluorobenzoylimidazole

A three-necked flask fitted with magnetic stirrer, thermometer, addition funnel, and nitrogen purge was charged with 2.72 g (40 mmol) imidazole and 70 ml of tetrahydrofuran. The resulting solution was stirred and cooled to −2° C., and 5.28 g of 80% assay chlorodifluoro-benzoic acid chloride (containing, therefore, 4.22 g or 20 mmol of desired starting material, the other 20% being residual toluene) dissolved in about 5 ml of tetrahydrofuran was then added dropwise over 0.5 hours with cooling. During this addition, the temperature dropped slowly to −10° C. After the addition was completed, the reaction mixture was allowed to come to room temperature.

The resulting slurry was stirred for 3 hours at room temperature and was then filtered to remove a white precipitate. The precipitate was washed with a small portion of tetrahydrofuran and was then discarded. The tetrahydrofuran solutions were combined, then concentrated at reduced pressure to give 5.0 g of an oil which upon standing yielded long needles. A slurry of 4 g of the needles in 12–15 ml of CCl$_4$ and 5 ml of CH$_2$Cl$_2$ was cooled to 0° C. and then filtered to separate the solids which were dried in a vacuum oven at 40° C. to give 1.91 g of the title compound, m.p. 80°–81° C. $^1$H NMR (CDCl$_3$, 300 MHz): 7.86 (s, 1H), 7.40 (m, 3H), 7.15 (d, 0.6 Hz, 1H). $^{13}$C NMR (CDCl$_3$): 161.7, 137.5, 131.9, 120.2 (C—F, J=21 Hz), 118.6 (C—F, J=20 Hz ).

Example 5

Methyl-3-(2-chloro-4,5-difluorophenyl)-3-oxopropionate

To a dry 1-liter 3-neck round bottom flask equipped with mechanical stirrer and nitrogen inlet was charged 67.7 grams (0.995 moles) imidazole and 1.5 liters of tetrahydrofuran. The solution was cooled to between 0° and 10° C. and was treated with 100 grams (0.474 moles) of 2-chloro-4,5-difluorobenzolyl chloride by moderately fast dropwise addition. The reaction mixture was allowed to warm to room temperature with stirring over a period of 1.5 hours. The resulting white precipitate of imidazole hydrochloride was removed by filtration while care was taken to maintain a nitrogen atmosphere throughout the operation. The filtrate was directly introduced to a second reaction flask of 2 liter capacity which was equipped with mechanical stirrer, condenser and nitrogen inlet and which contained 88.9 grams (0.569 moles) of the potassium salt of monomethylmalonate and 27 grams (0.284 moles) of dry magnesium chloride. The resulting mixture was heated to reflux for a period of eight hours and was then allowed to cool to room temperature. A 0.6 liter portion of water was added and the solution was adjusted to pH 1.0. The mixture was extracted with ethyl acetate (0.5 liters) and the organic phase was washed with an equal volume of saturated sodium bicarbonate solution. Finally, the organic phase was allowed to stand over dilute aqueous HCl adjusted to pH 1.0 for a period of 1 hour and then was dried over sodium sulfate. The solvent was evaporated and the solid residue was taken up in 2-propanol (60 ml) and was stirred for 15 minutes at room temperature followed by cooling to 0° C. The resulting solid was collected and dried. After collection of a second crop there was obtained 112 grams (95%) of the title compound. The material melted at 53° C. and had the following NMR spectrum indicative of the enol-form of this molecule: $^1$H NMR (CDCl$_3$, 300 MHz) : 7.48 (1H, dd, J=8.9 Hz, J=8.1 Hz), 7.3 (1H, dd, J=8.9, J=8.1 Hz), 5.62 (1H, s), 3.81 (3H, s). The infrared spectrum showed peaks at =3300, 3200–2400, 1640, 1600, 1560, 1500, 1340 cm$^{-1}$. Mass Spectrum: m/e 248 p+.

We claim:

1. A method for preparing a compound of the formula

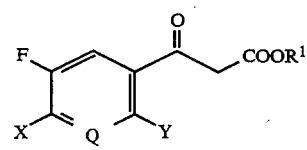

I said method comprising reacting a compound of the formula

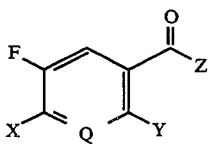

with a dianion of the formula

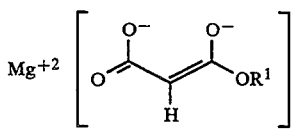

wherein Q is C—H or N; $R^1$ is $C_1$ to $C_6$ alkyl, benzyl or p-nitrobenzyl; X and Y are independently selected from fluoro and chloro; and Z is fluoro, chloro or bromo.

2. A method according to claim 1 wherein the dianion is obtained by reacting a monoanion of the formula

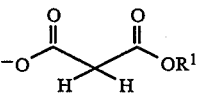

with a Grignard reagent of the formula $R^2MgW$; wherein $R^1$ is $C_1$ to $C_6$ alkyl, benzyl or p-nitrobenzyl; $R^2$ is $C_1$ to $C_4$ alkyl or phenyl; and W is chloro or bromo.

3. A method according to claim 2 wherein the reaction is conducted in a tetrahydrofuran solvent.

4. A method according to claim 2, wherein the preparation of the dianion is conducted in situ.

5. A method according to claim 2 wherein W is bromo.

6. A method according to claim 2 wherein W is chloro.

7. A method according to claim 6 wherein said Grignard reagent is $CH_3MgCl$.

* * * * *